US006589985B2

(12) United States Patent
Plata-Salaman et al.

(10) Patent No.: US 6,589,985 B2
(45) Date of Patent: Jul. 8, 2003

(54) CARBAMATE COMPOUNDS FOR USE IN PREVENTING OR TREATING MOVEMENT DISORDERS

(75) Inventors: Carlos R. Plata-Salaman, Ambler, PA (US); Boyu Zhao, Lansdale, PA (US); Roy E. Twyman, Doylestown, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/081,501

(22) Filed: Feb. 21, 2002

(65) Prior Publication Data

US 2002/0151585 A1 Oct. 17, 2002

Related U.S. Application Data

(60) Provisional application No. 60/271,683, filed on Feb. 27, 2001.

(51) Int. Cl.[7] ............................................... A61K 31/27
(52) U.S. Cl. ..................... 514/483; 514/488; 514/489
(58) Field of Search ............................... 514/483, 488, 514/489

(56) References Cited

U.S. PATENT DOCUMENTS

| | | |
|---|---|---|
| 3,265,728 A | 8/1966 | Bossinger et al. |
| 3,313,692 A | 4/1967 | Bossinger et al. |
| 5,854,283 A | 12/1998 | Choi et al. |
| 6,103,759 A | 8/2000 | Choi et al. |

OTHER PUBLICATIONS

Blandini, F., et al., *Movement Disorders*, Princ. Neural. Aging, 1997, 441–453.
Koller, W.C., et al., *Pharmacologic Treatment of Essential Tremor*, Neurology, 2000, 54(11, Suppl. 4), S30–S38.
Gasser, T., et al., *Genetics of Parkinson's Disease and Other Movement Disorders*, Neurogenetics, 2000, 351–372.
Collado–Seidel, V., et al., *Aetiology and Treatment of Restless Legs Syndrome*, CNS Drugs, 1999, 12(1), 9–20.
Bucher, S.F., et al., *Cerebral Generators Involved in the Pathogenesis of the Restless Legs Syndrome*, Annals of Neurology, 1997, 41(5), 639–645.
Kanazawa, I., *Extrapyramidal Tract Symptoms in Degenerative Diseases. Involuntary Movement in Degenerative Diseases, Huntington's Disease, Chorea–Acanthocytosis and Benign Hereditary Chorea*, Saishin Naikagaku Taikei, 1997, 68, 156–163 (with English translations).
Scheidt, C.E., *Psychosomatic Aspects of Idiopathic Spasmodic Torticollis. Results of a Multicenter Study*. Psychotherapie, Psychosomatik, Medizinische Psychologies, 1998, 48(1), 1–12, (with English translations).
Caligiuri, M.P., *Antipsychotic–induced Movement Disorders in the Elderly; Epidemiology and Treatment Recommentations*, Drugs Aging, 2000, 17(5), 363–384.

Poewe, W., *What is New in Movement Disorders*, Wien, Klin. Wochenschr., 1999, 111(17), 664–671.
Klein, C., et al., *Evaluation of the Role of the D2 Dopamine Receptor in Myoclonus Dystonia*, Ann. Neurol., 2000, 47(3), 369–373.
Ettore, B., *The Use of Anticonvulsants in Neurological Conditions other than Epilepsy: A Review of the Evidence from Randomized Controlled Trials*, CNS Drugs, 1999, 11(1), 61–82.
Tanner, C.M., *Epidemiology of Movement Disorders*, In: Anderson DW editor. Neuroepidemiology, CRC Press, 1991, 193–216.
Iwata, S., et al., *Effects of Beta–adrenergic Blockers on Drug–induced Tremors*, Biochem. Behav., 1993, 44(3), 611–613.
Galvez–Jimenez, N. and Hargreave, M., *Topiramate and Esstntial Tremor*, Ann. Neurol., 2000, 47(6), 837–838.
Gorman, W.P., et al., *A Comparison of Primidone, Propranolol in Essential Tremor, Using Quantitative Analysis*, J. Neurol. Neurosurg. Psychiatry, 1986, 49, 64–68.
Gironell, A., et al., *A Randomized Placebo–controlled Comparative Trial of Gabapentin and Propranolol in Essential Tremor*, Arch. Neurol., 1999, 56, 475–480.
Magnus, L., *Nonepileptic Uses of Gabapentin*, Epilepsia, 1999, 40(Suppl. 6), S66–72; 837–838.

(List continued on next page.)

Primary Examiner—William R. A. Jarvis

(57) ABSTRACT

This invention is directed to a method for preventing or treating movement disorders comprising administering to a subject in need thereof a therapeutically effective amount of a compound selected from the group consisting of Formula (I) and Formula (II):

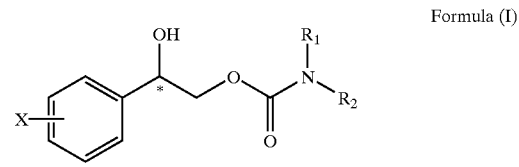

Formula (I)

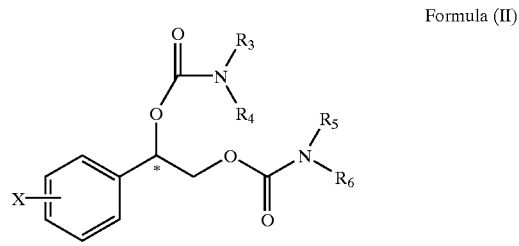

Formula (II)

wherein phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

23 Claims, No Drawings

OTHER PUBLICATIONS

Adler, C.H., *Treatment of Restless Legs Syndrome with Gabapentin*, Clin. Neuropharmacol., 1997, 20(2), 148–151.

Merren, M.D., *Gabapentin for Treatment of Pain and Tremor: A Large Case Series*, South Med. J., 1998, Aug., 91 (8) 739–744.

Wetter, T.C., Pollmacher, T., *Restless Legs and Periodic Leg Movements in Sleep Syndromes*, J. Neurol., 1997, Apr., 244 (4 Supp 1), S37–45).

PCT International Search Report PCT/US02/05542 dated Jul. 9, 2002.

U.S. patent application Ser. No. 09/906,251, Ortho–McNeil Pharmaceutical, Inc.

U.S. patent application Ser. No. 10/081,713, Ortho–McNeil Pharmaceutical, Inc.

U.S. patent application Ser. No. 10/081,766, Ortho–McNeil Pharmaceutical, Inc.

U.S. patent application Ser. No. 10/081,606, Ortho–McNeil Pharmaceutical, Inc.

U.S. patent application Ser. No. 10/081,761, Ortho–McNeil Pharmaceutical, Inc.

U.S. patent application Ser. No. 10/192,973, Ortho–McNeil Pharmaceutical, Inc.

U.S. patent application Ser. No. 10/081,943, Ortho–McNeil Pharmaceutical, Inc.

U.S. patent application Ser. No. 10/193,600, Ortho–McNeil Pharmaceutical, Inc.

U.S. patent application Ser. No. 10/081,764, Ortho–McNeil Pharmaceutical, Inc.

CARBAMATE COMPOUNDS FOR USE IN PREVENTING OR TREATING MOVEMENT DISORDERS

CROSS REFERENCE TO RELATED APPLICATIONS

This application claims benefit of provisional application Serial No. 60/271,683, filed Feb. 27, 2001, which is hereby incorporated by reference.

FIELD OF THE INVENTION

This invention is directed to a method for use of a carbamate compound in preventing or treating movement disorders. More particularly, this invention is directed to a method for use of halogenated 2-phenyl-1,2-ethanediol monocarbamate or dicarbamate compounds for preventing or treating movement disorders.

BACKGROUND OF THE INVENTION

Movement disorders are a broad group of disorders without a single underlying cause, resulting from a variety of neurological dysfunctions directly or indirectly linked to neuronal damage or abnormalities in nervous system pathways (Blandini F, et. al., Movement disorders, *Princ. Neural. Aging*, 1997, 441–453; Koller W C, et. al., Pharmacologic treatment of essential tremor, *Neurology*, 2000, 54 (11, Suppl. 4), S30–S38; Gasser T, et. al., Genetics of Parkinson's disease and other movement disorders, *Neurogenetics*, 2000, 351–372; Collado-Seidel V, et. al., Aetiology and treatment of restless legs syndrome, CNS *Drugs*, 1999, 12 (1), 9–20; Bucher S F, et. al., Cerebral generators involved in the pathogenesis of the restless legs syndrome, *Annals of Neurology*, 1997, 41 (5), 639–45; Kanazawa I, Extrapyramidal tract symptoms in degenerative diseases. Involuntary movement in degenerative diseases. Huntington's disease, chorea-acanthocytosis and benign hereditary chorea. *Saishin Naikagaku Taikei*, 1997, 68, 156–163; Scheidt C E, Psychosomatic aspects of idiopathic spasmodic torticollis. Results of a multicenter study. *Psychotherapie, Psychosomatik, Medizinische Psychologie*, 1998, 48 (1), 1–12; Caligiuri M P, Antipsychotic-induced movement disorders in the elderly: epidemiology and treatment recommendations, *Drugs Aging*, 2000, 17 (5), 363–384; Poewe W, What is new in movement disorders, *Wien. Klin. Wochenschr.*, 1999, 111 (17), 664–671; Klein C, et. al., Evaluation of the role of the D2 dopamine receptor in myoclonus dystonia, *Ann. Neurol.*, 2000, 47 (3), 369–373).

Such movement disorders include, but are not limited to, benign essential tremor (ET), tremor in Parkinson's disease (PD) and Parkinsonism, other non-related ET or PD tremors (such as head/limb resting, simple kinetic and intention, postural-associated, position-associated, orthostatic, enhanced physiologic, psychogenic, task-associated, voice, cerebellar, rubral and other central and non-classical tremors), restless leg syndrome (RLS), restless arm syndrome (RAS), chorea in Huntington's disease, idiopathic torsion dystonia, focal torsion dystonia, myoclonus, athetosis, abnormal movements in Wilson's disease, Gilles de La Tourette's syndrome, paroxysmal movement disorders (including paroxysmal dystonia (eg, kinesgenic paroxystic choreoathetosis, dystonic paroxystic choreoathetosis, intermediate paroxystic choreoathetosis and nocturnal paroxystic choreoathetosis), paroxystic ataxia and paroxystic tremor), post-anoxic spasms, post-spinal cord injury spasms, multiple sclerosis-associated tremor and drug-induced tremors and movement disorders (including, and not limited to, postural tremor, acute dystonia, chorea, akathisia, tardive dyskinesia and Parkinson's-like syndromes).

Antiepileptic drugs have been used to treat a variety of nonepileptic conditions including movement disorders (Ettore B, The use of anticonvulsants in neurological conditions other than epilepsy: A review of the evidence from randomized controlled trials, *CNS Drugs*, 1999, 11 (1), 61–82). Essential tremor is a common disorder with oscillating movements that often causes functional disability, potentially leading to physiological and emotional difficulties. Its prevalence is about 3.5–55 per 1000 population (Tanner C M, Epidemiology of Movement disorders. In: Anderson D W editor. *Neuroepidemiology*, CRC Press, 1991, 193–216). Beta-receptor blocking agents (propranolol and analogues) are a line of therapy for essential tremor (Iwata S, et. al., Effects of beta-adrenergic blockers on drug-induced tremors, *Biochem. Behav.*, 1993, 44 (3), 611–13). However, in addition to the incomplete clinical response, beta-receptor blocking agents are contraindicated in asthma, heart block, or congestive heart failure and must be used judiciously in patients with diabetes mellitus or recurrent depression.

In various conditions, anticonvulsants (such as carbamazepine, gabapentin and topiramate) may be effective in treating essential tremor. Topiramate given to nine patients with essential tremor may be useful for the management of essential tremor, especially in patients partially responsive to other established forms of treatment (Galvez-Jimenez N and Hargreave M, Topiramate and essential tremor, *Ann. Neurol*, 2000, 47 (6), 837–838). Eight patients rated themselves as better and with less disability after topiramate therapy. One patient reported increased diuresis while receiving topiramate. The most common side effects were fatigue and paresthesias. Gabapentin, an antiepileptic, has been used for treating essential tremor (Koller W C, Pharmacologic treatment of essential tremor, *Neurology*, 2000, 54 (11), (Suppl. 4), S30–S38). In an open-label report, gabapentin reduced tremor in five patients. Three of the patients elected to remain on gabapentin as opposed to their previous medication. Carbamazepine and gabapentin have shown effectiveness in treating essential tremor (Ettore B, The use of anticonvulsants in neurological conditions other than epilepsy: A review of the evidence from randomized controlled trials, *CNS Drugs*, 1999, 11 (1), 61–82). Other anticonvulsants may also be effective in treating essential tremor (Koller W C, Pharmacologic treatment of essential tremor, *Neurology*, 2000, 54 (11), (Suppl. 4), S30–S38; Gorman W P, et. al., A comparison of primidone, propranolol in essential tremor, using quantitative analysis, *J. Neurol. Neurosurg. Psychiatry*, 1986; 49, 64–68; Gironell A, et. Al., A randomized placebo-controlled comparative trial of gabapentin and propranolol in essential tremor, *Arch. Neurol.*, 1999, 56, 475; Leslie M, Nonepileptic uses of gabapentin, *Epilepsia*, 1999, 40 (Suppl. 6), S66–S72; 837–838; Ettore B, The use of anticonvulsants in neurological conditions other than epilepsy: A review of the evidence from randomized controlled trials, *CNS Drugs*, 1999, 11 (1), 61–82).

RLS and RAS are common, chronic disorders characterized by a need to move the legs or arms, especially when relaxed. These neurological movement disorders also affect induction of sleep and can become a significant source of sleep-disturbance because of the compulsive movement of the extremities; such disorders and consequences can also be associated with paresthesias and excessive daytime tiredness. There is 1–5% prevalence of these disorders in the general population and 15% in the medical population. The etiology of RLS remains unknown. Levodopa/decarboxylase inhibitors (carbidopa, benserazide) and dopamine agonists are regarded as a line of treatment for RLS. The development of time shift and/or augmentation of symptoms is a major problem with dopaminergic treatment. Importantly, anticonvulsants such as gabapentin and carbamazepine also have efficacy in RLS (Adler C H, Treatment of restless legs syndrome with gabapentin, *Clin. Neuropharmacol.*, 1997, 20 (2), 148–151; Merren M D, Gabapentin for treatment of pain and tremor: a large case series, *South Med. J.*, 1998 Aug, 91 (8), 739–44; Wetter T C, Pollmacher T, Restless legs and periodic leg movements in sleep syndromes, *J. Neurol*, 1997 Apr, 244 (4 Suppl 1), S37–45). The efficacy of anticonvulsants in movement disorders such as essential tremor and RLS is thought to be due, in part, to the neurostabilizing properties of this class of drugs, which may restore the imbalance in the generation and transmission of motor impulses.

Substituted phenyl alkyl carbamate compounds have been described in U.S. Pat. No. 3,265,728 to Bossinger, et al (hereby incorporated by reference), as useful in treating the central nervous system, having tranquilization, sedation and muscle relaxation properties of the formula:

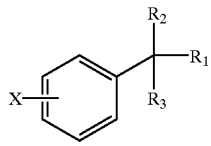

wherein $R_1$ is either carbamate or alkyl carbamate containing from 1 to 3 carbon atoms in the alkyl group; $R_2$ is either hydrogen, hydroxy, alkyl or hydroxy alkyl containing from 1 to 2 carbons; $R_3$ is either hydrogen or alkyl containing from 1 to 2 carbons; and X can be halogen, methyl, methoxy, phenyl, nitro or amino.

A method for inducing calming and muscle relaxation with carbamates has been described in U.S. Pat. No. 3,313,692 to Bossinger, et al (hereby incorporated by reference) by administering a compound of the formula:

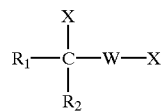

in which W represents an aliphatic radical containing less than 4 carbon atoms, wherein $R_1$ represents an aromatic radical, $R_2$ represents hydrogen or an alkyl radical containing less than 4 carbon atoms, and X represents hydrogen or hydroxy or alkoxy and alkyl radicals containing less than 4 carbon atoms or the radical:

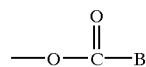

in which B represents an organic amine radical of the group consisting of heterocyclic, ureido and hydrazino radicals and the radical —N($R_3$)$_2$ wherein $R_3$ represents hydrogen or an alkyl radical containing less than 4 carbon atoms.

Optically pure forms of halogen substituted 2-phenyl-1,2-ethanediol monocarbamates and dicarbamates have also been described in U.S. Pat. No. 6,103,759 to Choi, et al (hereby incorporated by reference), as effective for treating and preventing central nervous system disorders including convulsions, epilepsy, stroke and muscle spasm; and as useful in the treatment of central nervous system diseases, particularly as anticonvulsants, antiepileptics, neuroprotective agents and centrally acting muscle relaxants, of the formulae:

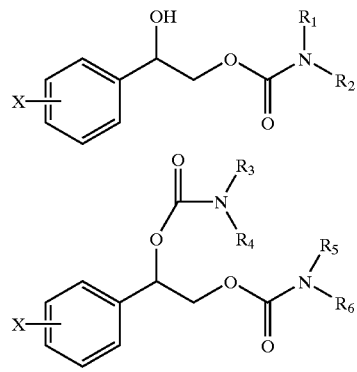

wherein one enantiomer predominates and wherein the phenyl ring is substituted at X with one to five halogen atoms selected from fluorine, chlorine, bromine or iodine atoms and $R_1$, $R_2$, $R_3$, $R_4$, $R_5$ and $R_6$ are each selected from hydrogen and straight or branched alkyl groups with one to four carbons optionally substituted with a phenyl group with substituents selected from the group consisting of hydrogen, halogen, alkyl, alkyloxy, amino, nitro and cyano. Pure enantiomeric forms and enantiomeric mixtures were described wherein one of the enantiomers predominates in the mixture for the compounds represented by the formulae above; preferably one of the enantiomers predominates to the extent of about 90% or greater; and, most preferably, about 98% or greater.

Halogen substituted 2-phenyl-1,2-ethanediol carbamate compounds of Formula (I) or Formula (II) have not been previously described as useful for preventing or treating movement disorders. Recent preclinical studies have revealed previously unrecognized pharmacological properties which suggest that a compound of Formula (I) or Formula (II) is useful in preventing or treating movement disorders. Therefore, it is an object of the present invention to teach a method for use of a compound of Formula (I) or Formula (II) in preventing or treating movement disorders.

SUMMARY OF THE INVENTION

The present invention is directed to a method for preventing or treating movement disorders comprising administering to a subject in need thereof a therapeutically effective amount of a compound selected from the group consisting of Formula (I) and Formula (II):

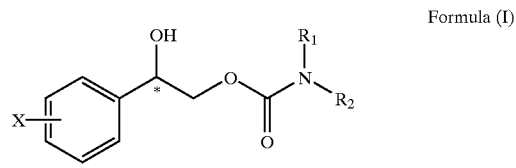

Formula (I)

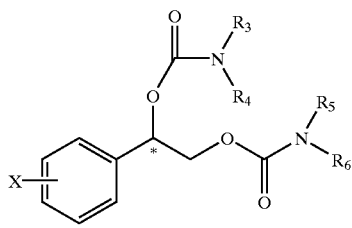

Formula (II)

wherein phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

Embodiments of the invention include a method for preventing or treating movement disorders comprising administering to a subject in need thereof a therapeutically effective amount of a pharmaceutical composition comprising a pharmaceutically acceptable carrier and a compound selected from the group consisting of Formula (I) and Formula (II).

Embodiments of the invention include the use of a compound selected from the group consisting of Formula (I) and Formula (II) for the preparation of a medicament for preventing or treating movement disorders in a subject in need thereof.

Embodiments of the method include the use of an enantiomer selected from the group consisting of Formula (I) and Formula (II) or enantiomeric mixture wherein one enantiomer selected from the group consisting of Formula (I) and Formula (II) predominates. For enantiomeric mixtures wherein one enantiomer selected from the group consisting of Formula (I) and Formula (II) predominates, preferably, one enantiomer selected from the group consisting of Formula (I) and Formula (II) predominates to the extent of about 90% or greater. More preferably, one enantiomer selected from the group consisting of Formula (I) and Formula (II) predominates to the extent of about 98% or greater.

DETAILED DESCRIPTION OF THE INVENTION

The present invention is directed to a method for preventing or treating movement disorders comprising administering to a subject in need thereof a therapeutically effective amount of a compound selected from the group consisting of Formula (I) and Formula (II):

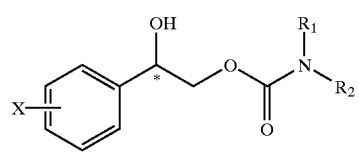

Formula (I)

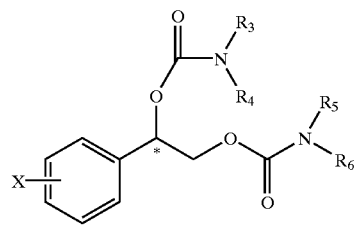

Formula (II)

wherein phenyl is substituted at X with one to five halogen atoms selected from the group consisting of fluorine, chlorine, bromine and iodine; and, $R_1$, $R_2$, $R_3$, $R_4$, $R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

The present method includes the use of a compound selected from the group consisting of Formula (I) and Formula (II) wherein X is chlorine; preferably, X is substituted at the ortho position of the phenyl ring.

The present method also includes the use of a compound selected from the group consisting of Formula (I) and Formula (II) wherein $R_1$, $R_2$, $R_3$, $R_4$, $R_5$ and $R_6$ are preferably selected from hydrogen.

An embodiment of the present method includes the use of an enantiomer selected from the group consisting of Formula (I) and Formula (II) or enantiomeric mixture wherein one enantiomer selected from the group consisting of Formula (I) and Formula (II) predominates wherein X is chlorine; preferably, X is substituted at the ortho position of the phenyl ring.

The present method also includes the use of an enantiomer selected from the group consisting of Formula (I) and Formula (II) or enantiomeric mixture wherein one enantiomer selected from the group consisting of Formula (I) and Formula (II) predominates wherein $R_1$, $R_2$, $R_3$, $R_4$, $R_5$ and $R_6$ are preferably selected from hydrogen.

For enantiomeric mixtures wherein one enantiomer selected from the group consisting of Formula (I) and Formula (II) predominates, preferably, an enantiomer selected from the group consisting of Formula (I) and Formula (II) predominates to the extent of about 90% or greater. More preferably, an enantiomer selected from the group consisting of Formula (I) and Formula (II) predominates to the extent of about 98% or greater.

An embodiment of the present method includes the use of an enantiomer selected from the group consisting of Formula (Ia) and Formula (IIa) or enantiomeric mixture wherein one enantiomer selected from the group consisting of Formula (Ia) and Formula (IIa) predominates:

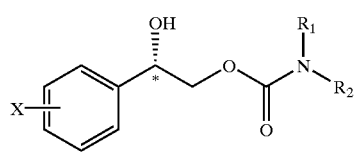

Formula (Ia)

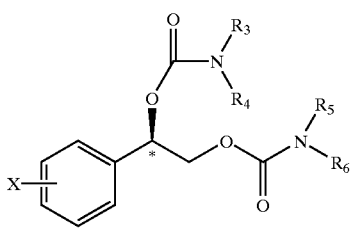

Formula (IIa)

wherein phenyl is substituted at X with one to five halogen atoms selected from the group consisting of fluorine, chlorine, bromine and iodine; and, $R_1, R_2, R_3, R_4, R_5$ and $R_6$ are independently selected from the group consisting of hydrogen and $C_1$–$C_4$ alkyl; wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

The present method includes the use of an enantiomer selected from the group consisting of Formula (Ia) and Formula (IIa) or enantiomeric mixture wherein one enantiomer selected from the group consisting of Formula (Ia) and Formula (IIa) predominates wherein X is chlorine; preferably, X is substituted at the ortho position of the phenyl ring.

The present method also includes the use of an enantiomer selected from the group consisting of Formula (Ia) and Formula (IIa) or enantiomeric mixture wherein one enantiomer selected from the group consisting of Formula (Ia) and Formula (IIa) predominates wherein $R_1, R_2, R_3, R_4, R_5$ and $R_6$ are preferably selected from hydrogen.

For enantiomeric mixtures wherein one enantiomer selected from the group consisting of Formula (Ia) and Formula (IIa) predominates, preferably, an enantiomer selected from the group consisting of Formula (Ia) and Formula (IIa) predominates to the extent of about 90% or greater. More preferably, an enantiomer selected from the group consisting of Formula (Ia) and Formula (IIa) predominates to the extent of about 98% or greater.

An embodiment of the present method includes a method for preventing or treating movement disorders comprising administering to a subject in need thereof a therapeutically effective amount of an enantiomer selected from the group consisting of Formula (Ib) and Formula (IIb) or enantiomeric mixture wherein one enantiomer selected from the group consisting of Formula (Ib) and Formula (IIb) predominates:

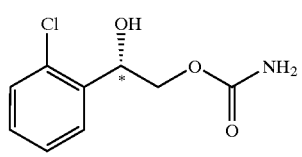

Formula (Ib)

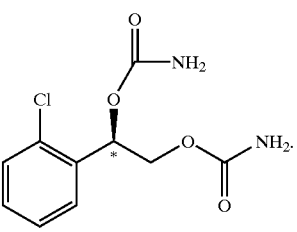

Formula (IIb)

For enantiomeric mixtures wherein one enantiomer selected from the group consisting of Formula (Ib) and Formula (IIb) predominates, preferably, an enantiomer selected from the group consisting of Formula (Ib) and Formula (IIb) predominates to the extent of about 90% or greater. More preferably, an enantiomer selected from the group consisting of Formula (Ib) and Formula (IIb) predominates to the extent of about 98% or greater.

Other crystal forms of the present invention may exist and as such are intended to be included in the present invention.

It is apparent to those skilled in the art that the compounds of the invention are present as racemates, enantiomers and enantiomeric mixtures thereof. A carbamate enantiomer selected from the group consisting of Formula (I), Formula (II), Formula (Ia), Formula (IIa), Formula (Ib) and Formula (IIb) contains an asymmetric chiral carbon atom at the benzylic position, which is the aliphatic carbon adjacent to the phenyl ring (represented by the asterisk in the structural formulae).

Compounds of the present invention may be prepared as described in the previously referenced Bossinger '728 patent (incorporated by reference), Bossinger '692 patent (incorporated by reference) and Choi '759 patent (incorporated by reference).

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The present invention contemplates a method for preventing or treating movement disorders in a subject in need thereof. Movement disorders include, and are not limited to, benign essential tremor, tremor in Parkinson's disease, Parkinsonism tremor, other non-related essential tremors, other non-related Parkinsonism tremors (other non-related essential or Parkinsonism tremors include central tremors and non-classic tremors (wherein central and non-classic tremors include, but are not limited to, head/limb resting tremor, simple kinetic tremor, intention tremor, orthostatic tremor, enhanced physiologic tremor, psychogenic tremor, cerebellar tremor, rubral tremor or tremors associated with posture, position, voice or task)), drug-induced tremors and movement disorders (including, but not limited to, postural tremor, acute dystonia, chorea, akathisia, tardive dyskinesia or Parkinson's-like syndromes), restless leg syndrome, restless arm syndrome, chorea in Huntington's disease, tremors associated with multiple sclerosis or Gilles de La Tourette's syndrome, post-spinal cord injury spasms, post-anoxic spasms, idiopathic torsion dystonia, focal torsion dystonia, myoclonus, athetosis, paroxysmal movement disorders (such as paroxysmal dystonia, paroxystic ataxia and paroxystic tremors) or abnormal movements (such as in Wilson's disease).

An example of the method of the present invention comprises administering to the subject a therapeutically effective amount of a compound selected from the group consisting of Formula (I) and Formula (II) in a pharmaceutical composition comprising a pharmaceutically acceptable carrier and a compound selected from the group consisting of Formula (I) and Formula (II). The method of the present invention also includes the use of a compound selected from the group consisting of Formula (I) and Formula (II) for the preparation of a medicament for preventing or treating movement disorders.

Another example of the method of the present invention comprises administering to the subject a therapeutically effective amount of a compound selected from the group consisting of Formula (I) and Formula (II) or a pharmaceutical composition thereof in combination with one or more agents useful in preventing or treating movement disorders.

A compound selected from the group consisting of Formula (I) and Formula (II) or pharmaceutical composition thereof may be administered by any conventional route of administration including, but not limited to oral, pulmonary, intraperitoneal (ip), intravenous (iv), intramuscular (im), subcutaneous (sc), transdermal, buccal, nasal, sublingual, ocular, rectal and vaginal. In addition, administration directly to the nervous system may include, and are not limited to, intracerebral, intraventricular, intracerebroventricular, intrathecal, intracisternal, intraspinal or peri-spinal routes of administration by delivery via intracranial or intravertebral needles or catheters with or without pump devices. It will be readily apparent to those skilled in the art that any dose or frequency of administration that provides the therapeutic effect described herein is suitable for use in the present invention.

The therapeutically effective amount of a compound selected from the group consisting of Formula (I) and Formula (II) or pharmaceutical composition thereof may be from about 0.01 mg/Kg/dose to about 100 mg/Kg/dose. Preferably, the therapeutically effective amount may be from about 0.01 mg/Kg/dose to about 25 mg/Kg/dose. More preferably, the therapeutically effective amount may be from about 0.01 mg/Kg/dose to about 10 mg/Kg/dose. Most preferably, the therapeutically effective amount may be from about 0.01 mg/Kg/dose to about 5 mg/Kg/dose. Therefore, the therapeutically effective amount of the active ingredient contained per dosage unit (e.g., tablet, capsule, powder, injection, suppository, teaspoonful and the like) as described herein may be from about 1 mg/day to about 7000 mg/day for a subject, for example, having an average weight of 70 Kg.

The dosages, however, may be varied depending upon the requirement of the subjects (including factors associated with the particular subject being treated, including subject age, weight and diet, strength of the preparation, the advancement of the disease condition and the mode and time of administration) and the use of a particular compound of Formula (I) or Formula (II) or pharmaceutical composition thereof.

Optimal dosages to be administered may be readily determined by those skilled in the art and will result in the need to adjust the dose to an appropriate therapeutic level. The use of either daily administration or post-periodic dosing may be employed. Preferably, a compound of Formula (I) or Formula (II) or pharmaceutical composition thereof for preventing or treating movement disorders is administered orally or parenterally.

In accordance with the methods of the present invention, a compound of Formula (I) or Formula (II) or pharmaceutical composition thereof described herein may be administered separately, at different times during the course of therapy or concurrently in divided combination or single combination forms. Advantageously, a compound selected from the group consisting of Formula (I) and Formula (II) or pharmaceutical compositions thereof may be administered in a single daily dose or the total daily dosage may be administered via continuous delivery or in divided doses of two, three or four times daily. The instant invention is therefore to be understood as embracing all such methods and regimes of continuous, simultaneous or alternating treatment and the term "administering" is to be interpreted accordingly.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

As used herein, the term "composition" is intended to encompass a product comprising the specified ingredients in the specified amounts, as well as any product which results, directly or indirectly, from combinations of the specified ingredients in the specified amounts.

To prepare a pharmaceutical composition of the present invention, a compound of Formula (I) or Formula (II) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients,* published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded,* Volumes 1–3, edited by Lieberman et al; *Pharmaceutical Dosage Forms: Parenteral Medications,* Volumes 1–2, edited by Avis et al; and *Pharmaceutical Dosage Forms: Disperse Systems,* Volumes 1–2, edited by Lieberman et al; published by Marcel Dekker, Inc.

Preferably, a pharmaceutical composition is in a unit dosage form such as a tablet, pill, capsule, caplet, gelcap, lozenge, granule, powder, sterile parenteral solution or suspension, metered aerosol or liquid spray, drop, ampoule, autoinjector device or suppository for administration by oral, intranasal, sublingual, intraocular, transdermal, parenteral, rectal, vaginal, inhalation or insufflation means. Alternatively, the composition may be presented in a form suitable for once-weekly or once-monthly administration or may be adapted to provide a preparation for intramuscular injection.

In preparing a pharmaceutical composition having a solid dosage form for oral administration, such as a tablet, pill, capsule, caplet, gelcap, lozenge, granule or powder (each including immediate release, timed release and sustained release formulations), suitable carriers and additives include but are not limited to diluents, granulating agents, lubricants, binders, glidants, disintegrating agents and the like. If desired, tablets may be sugar coated, gelatin coated, film coated or enteric coated by standard techniques.

For preparing a solid dosage form, the principal active ingredient is mixed with a pharmaceutical carrier (e.g. conventional tableting ingredients such as diluents, binders, adhesives, disintegrants, lubricants, antiadherents and glidants). Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

In preparing a pharmaceutical composition having a liquid dosage form for oral, topical and parenteral administration, any of the usual pharmaceutical media or excipients may be employed. Thus, for liquid unit dosage forms, such as suspensions (i.e. colloids, emulsions and dispersions) and solutions, suitable carriers and additives include but are not limited to pharmaceutically acceptable wetting agents, dispersants, flocculation agents, thickeners, pH control agents (i.e. buffers), osmotic agents, coloring agents, flavors, fragrances, preservatives (i.e. to control microbial growth, etc.) and a liquid vehicle may be employed. Not all of the components listed above will be required for each liquid dosage form. The liquid forms in which the novel compositions of the present invention may be incorporated for administration orally or by injection include, but are not limited to aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles.

BIOLOGICAL EXPERIMENTAL EXAMPLE

The activity of a compound of Formula (I) or Formula (II) for use in preventing or treating movement disorders was evaluated in the following experimental example which is intended to be a way of illustrating but not limiting the invention.

Harmaline-Induced Tremors in Rats

Harmaline, a β-carboline derivative, is well known to produce tremor through a direct activation of cells in the inferior olive although the receptor(s) through which harmaline acts remains unknown. Harmaline-induced tremor in rats is a commonly accepted animal model that is predictive of essential tremor and related movement disorders in human (Miwa H, et. al., Differential expression of c-Fos following administration of two tremorgenic agents: harmaline and oxotremorine, *NeuroReport*, 2000, 11 (11), 2385–2390; Stanford J A and Fowler S C, At low doses, harmaline increases forelimb tremor in the rat, *Neurosci. Lett.*, 1998, 241 (1), 41–44; Sinton C M, The effectiveness of different isomers of octanol as blockers of harmaline-induced tremor, *Pfluegers Arch.*, 1989, 414 (1), 31–6).

An enantiomer of Formula (Ib) was evaluated for efficacy in treating essential tremor and related movement disorders with doses up to 30 mg/kg. The enantiomer of Formula (Ib) or vehicle (0.5% hydroxypropyl methylcellulose) was administered orally by gavage in a dose volume equivalent to 5 mL/kg to Sprague-Dawley rats (135 to 275 g). Harmaline (6 mg/kg in volume of 5 mL/kg, i.p.) was administered 60 min thereafter. Immediately after the harmaline administration, rats were placed individually in a blinded fashion in plastic cages on wood-chip bedding and observed for 30 minutes. Appearance of tremors was scored using a nine-item checklist. The checklist includes scoring for: tremors at rest, tremors during locomotion, intermittent tremors, continuous tremors, tremors provoked by tail-restraint, generalized tremors (head, body and tail), tremors of the head only, tremors of the body only and tremors of the tail only. Signs observed in rats treated with vehicle or test compound are compared by ranking tremor quality and severity.

Since rats that exhibit tremors at rest also exhibit tremors while moving, tremors that appear during rest were assigned a score =2, while tremors that only appear during locomotion were assigned a score =1. Tremor provoked following tail-restraint was assigned a score =1. Tremors that appear continuously were assigned a score =2, while tremors that appear intermittently were assigned a score =1. The appearance of generalized tremors were assigned a score =2, while a score =1 was assigned to tremor that involves only the head, body or tail of the rat. The severity of tremor is scored subjectively as mild in intensity or as moderate or marked. When the severity of tremor was considered moderate or marked, the score was assigned as described above. When the severity of tremor was considered mild, the score that was assigned was one-half of that described above. Scores for each rat were summed; the sum of the scores (between groups of rats treated with either the vehicle or test compound) were compared by ranking tremor quality and severity.

Statistical analysis of these data was performed by a Kruskal-Wallis nonparametric one-way method using JMP, Version 3 (SAS Institute, Inc.). The results indicate that the reduction in the tremor score in drug-treated groups compared to the vehicle-treated group was significant, suggesting that an enantiomer of Formula (Ib) is efficacious in treating essential tremor and related movement disorders.

Table 1 summarizes the experimental data (n is the number of animals per group and p value is based on comparison with vehicle).

TABLE 1

Formula (Ib) Tremor Score

| Dose | | Tremor Score | |
|---|---|---|---|
| (mg/kg, p.o.) | n | Median | p value |
| Vehicle | 9 | 6.00 | |
| 20 | 6 | 2.00 | <0.01 |
| 30 | 6 | 1.20 | <0.01 |

While the foregoing specification teaches the principles of the present invention, with examples provided for the purposes of illustration, it will be understood that the practice of the invention encompasses all of the usual variations, adaptations and/or modifications as come within the scope of the following claims and their equivalents.

What is claimed is:

1. A method for preventing or treating movement disorders comprising administering to a subject in need thereof a therapeutically effective amount of a compound selected from the group consisting of Formula (I) and Formula (II):

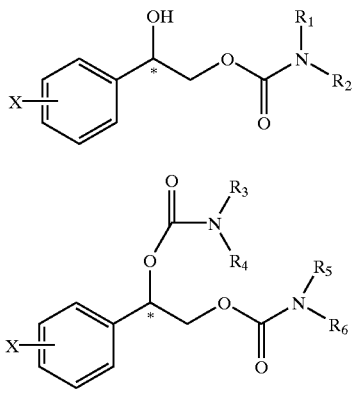

Formula (I)

Formula (II)

wherein
  phenyl is substituted at X with one to five halogen atoms selected from the group consisting of fluorine, chlorine, bromine and iodine; and,
  $R_1$, $R_2$, $R_3$, $R_4$, $R_5$ and $R_6$ are independently selected from the group consisting of hydrogen and $C_1$–$C_4$ alkyl;
  wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

2. The method of claim 1 wherein X is chlorine.

3. The method of claim 1 wherein X is substituted at the ortho position of the phenyl ring.

4. The method of claim 1 wherein $R_1$, $R_2$, $R_3$, $R_4$, $R_5$ and $R_6$ are selected from hydrogen.

5. A method for preventing or treating movement disorders comprising administering to a subject in need thereof a therapeutically effective amount of an enantiomer selected from the group consisting of Formula (I) and Formula (II) or enantiomeric mixture wherein one enantiomer selected from the group consisting of Formula (I) and Formula (II) predominates:

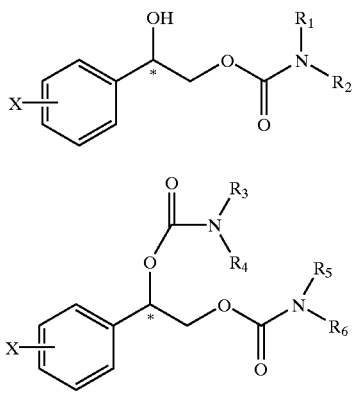

Formula (I)

Formula (II)

wherein
  phenyl is substituted at X with one to five halogen atoms selected from the group consisting of fluorine, chlorine, bromine and iodine; and,
  $R_1$, $R_2$, $R_3$, $R_4$, $R_5$ and $R_6$ are independently selected from the group consisting of hydrogen and $C_1$–$C_4$ alkyl;
  wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

6. The method of claim 5 wherein X is chlorine.

7. The method of claim 5 wherein X is substituted at the ortho position of the phenyl ring.

8. The method of claim 5 wherein $R_1$, $R_2$, $R_3$, $R_4$, $R_5$ and R6 are selected from hydrogen.

9. The method of claim 5 wherein one enantiomer selected from the group consisting of Formula (I) and Formula (II) predominates to the extent of about 90% or greater.

10. The method of claim 5 wherein one enantiomer selected from the group consisting of Formula (I) and Formula (II) predominates to the extent of about 98% or greater.

11. The method of claim 5 wherein the enantiomer selected from the group consisting of Formula (I) and Formula (II) is an enantiomer selected from the group consisting of Formula (Ia) and Formula (IIa):

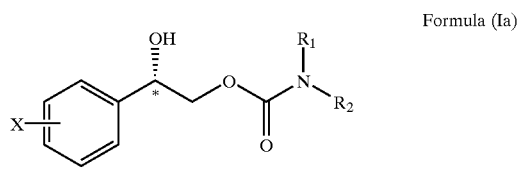

Formula (Ia)

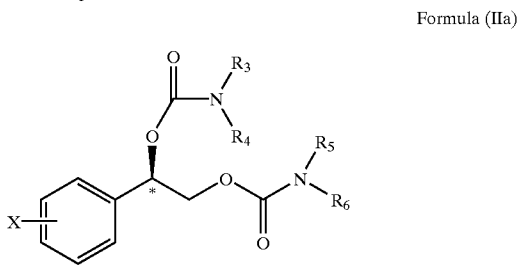

Formula (IIa)

wherein
  phenyl is substituted at X with one to five halogen atoms selected from the group consisting of fluorine, chlorine, bromine and iodine; and,
  $R_1$, $R_2$, $R_3$, $R_4$, $R_5$ and $R_6$ are independently selected from the group consisting of hydrogen and $C_1$–$C_4$ alkyl;
  wherein $C_1$–$C_4$ alkyl is optionally substituted with phenyl (wherein phenyl is optionally substituted with substituents independently selected from the group consisting of halogen, $C_1$–$C_4$ alkyl, $C_1$–$C_4$ alkoxy, amino, nitro and cyano).

12. The method of claim 11 wherein X is chlorine.

13. The method of claim 11 wherein X is substituted at the ortho position of the phenyl ring.

14. The method of claim 11 wherein $R_1$, $R_2$, $R_3$, $R_4$, $R_5$ and $R_6$ are selected from hydrogen.

15. The method of claim 11 wherein one enantiomer selected from the group consisting of Formula (Ia) and Formula (IIa) predominates to the extent of about 90% or greater.

16. The method of claim 11 wherein one enantiomer selected from the group consisting of Formula (Ia) and Formula (IIa) predominates to the extent of about 98% or greater.

17. The method of claim 5 wherein the enantiomer selected from the group consisting of Formula (I) and Formula (II) is an enantiomer selected from the group consisting of Formula (Ib) and Formula (IIb):

Formula (Ib)

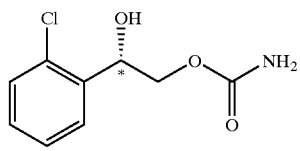

Formula (IIb)

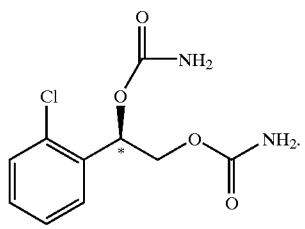

18. The method of claim 17 wherein one enantiomer selected from the group consisting of Formula (Ib) and Formula (IIb) predominates to the extent of about 90% or greater.

19. The method of claim 17 wherein one enantiomer selected from the group consisting of Formula (Ib) and Formula (IIb) predominates to the extent of about 98% or greater.

20. The method as in claim 1 wherein movement disorders are selected from benign essential tremor, tremor in Parkinson's disease, Parkinsonism tremor, other non-related essential tremors, other non-related Parkinsonism tremors, drug-induced tremors and movement disorders, restless leg syndrom, restless arm syndrom, chorea in Huntington's disease, tremors associated with multiple sclerosis or Gilles de La Tourette's syndrom, post-spinal cord injury spasms, post-anoxic spasm, idiopathic torsion dystonia, focal torsion dystonia, myoclonus, athetosis, paroxysmal movement disorders (selected from paroxysmal dystonia, paroxystic ataxia or paroxystic tremors) or abnormal movements (selected from Wilson's disease).

21. The method of claim 20 wherein movement disorders are selected from benign essential tremor, tremor in Parkinson's disease, Parkinsonism tremor, other non-related essential tremors, other non-related Parkinsonism tremors, drug-induced tremors and movement disorders, restless leg syndrome, chorea in Huntington's disease, tremors associated with multiple sclerosis or Gilles de La Tourette's syndrome or post-spinal cord injury spasms.

22. The method of claim 21 wherein other non-related essential or non-related Parkinsonism tremors are selected from central tremors or non-classic tremors (wherein central and non-classic tremors are selected from head/limb resting tremor, simple kinetic tremor, intention tremor, orthostatic tremor, enhanced physiologic tremor, psychogenic tremor, cerebellar tremor, rubral tremor or tremors associated with posture, position, voice or task); and, wherein drug-induced tremors and movement disorders are selected from postural tremor, acute dystonia, chorea, akathisia, tardive dyskinesia or Parkinson's-like syndromes.

23. The method as in claim 1 wherein the therapeutically effective amount is from about 0.01 mg/Kg/dose to about 100 mg/Kg/dose.

* * * * *